United States Patent [19]

Nonoyama et al.

[11] Patent Number: 5,346,695
[45] Date of Patent: Sep. 13, 1994

[54] METHODS OF INHIBITING HIV REPLICATION IN VITRO USING POLYMERS OF P-HYDROXYLATED CINNAMIC ACIDS

[75] Inventors: Meihan Nonoyama, St. Petersburg; Akiko Tanaka; Patrick K. Lai, both of Clearwater, all of Fla.; Kunio Konno, Tokyo, Japan; Yutaka Kawazoe, Tokyo, Japan; Hiroshi Sakagami, Tokyo, Japan

[73] Assignee: Tampa Bay Research Institute, St. Petersburg, Fla.

[21] Appl. No.: 996,869

[22] Filed: Dec. 28, 1992

Related U.S. Application Data

[63] Continuation of Ser. No. 675,943, Mar. 27, 1991.

[51] Int. Cl.$^5$ .................. A61K 31/74; A61K 31/745
[52] U.S. Cl. .................. 424/78.08; 514/576; 526/318.1
[58] Field of Search ...................... 424/78.08

[56] References Cited

U.S. PATENT DOCUMENTS

| | | | |
|---|---|---|---|
| 4,049,798 | 9/1977 | Bottomley | 424/195 |
| 4,117,120 | 9/1978 | Elderbaum | 424/195 |
| 4,132,782 | 1/1979 | Bean | 424/195 |
| 4,185,097 | 1/1980 | Ward et al. | 424/195 |
| 4,230,725 | 10/1980 | Fukui et al. | 424/325 |
| 4,285,934 | 8/1981 | Tinnell | 424/148 |

OTHER PUBLICATIONS

Kreis et al Antiviral Res. 14, p. 323 (1990).
Suzuki et al BBRC 160 p. 367 (1989).
Sakagami et al BBRC 172 p. 1267 (1990).
Nagata et al., *Antiviral Research*, "Inhibition of Influenza Virus Infection by Pine Cone Antitumore Substances," 13:11-22 (1990).
Lai et al., *AIDS Research and Human Retroviruses*, "Modification of Human Immuno-Deficiency Viral Replication by Pine Cone," 6:205-217, (1990).
Schinazi et al., *Antimicrob. Agents Chemother.*, "Activities of 3'-Azido-3'-Deoxythymidine Nucleotide Dimers in Primary . . . " 34:1061-1066 (1990).
Cooley et al., *New England J. of Med.*, "Once daily Administration of 2'3'-Dideoxyinosine (ddI) in Patients with Acquired . . . " 322:1340-1345 (1990).

*Primary Examiner*—G. S. Kishore
*Attorney, Agent, or Firm*—Rothwell, Figg, Ernst & Kurz

[57] ABSTRACT

Polymers of p-hydroxylated cinnamic acids and p-hydroxylated cinnamyl alcohols have potent anti-viral activity in vitro.

5 Claims, 1 Drawing Sheet

METHODS OF INHIBITING HIV REPLICATION IN VITRO USING POLYMERS OF P-HYDROXYLATED CINNAMIC ACIDS

This invention was made with government support under a cooperative agreement UO1 AI 27280 awarded by the National Institutes of Health (NIH). The government has certain rights in the invention.

This is a continuation of application Ser. No. 07/675,943, filed Mar. 27, 1991, abandoned.

FIELD OF THE INVENTION

This invention is directed to active synthetic polymer agents having potent anti-viral activity. More specifically, the invention is directed to polymers of p-hydroxylated cinnamic acid, p-hydroxylated cinnamyl alcohol, and derivatives thereof having anti-viral activity, especially anti-HIV, anti-influenza and anti-Herpes Simplex virus activity.

BACKGROUND OF THE INVENTION

Vital infections can present significant health threats, causing serious illnesses and, in some instances, death. For example, Acquired Immune Deficiency Syndrome (AIDS) has become a significant public health threat in recent years. The virus believed to be the causative agent of AIDS has been described by several names. It has been known as lymphadenopathy-associated virus (LAV), AIDS-related virus (ARV) and human immunodeficiency virus (HIV). Within the last few years, scientists have discovered that there are at least two distinct viruses, HIV-1 and HIV-2. HIV-1 is the virus originally isolated in 1983 (*Ann. Virol. Inst. Pasteur,* 135E:119–134 [1986]); HIV-2 was isolated by researchers in 1986 (see *Nature,* 326:662 [1987]). As used herein, HIV refers to these viruses generically.

A number of synthetic compounds have been found to possess anti-HIV activity. Most, if not all, of these compounds are nucleotide analogs, such as azidothymidine (AZT) and dideoxyiosine (ddI). See, for example, *Science* 243: 1731 ( 1989 ); *Ann. Intern. Med.* 122:812 ( 1990 ); *Antimicrob. Agents Chemother.* 34:1061 (1990); and *N. E. J. Med.* 322:133 and 1340 (1990). Although these compounds are useful, additional compounds are sought.

Other viruses also present significant health risks. Influenza is an acute febrile viral illness that yearly spreads to epidemic proportions, and periodically occurs in worldwide or pandemic form. Human influenza viruses are divided on the basis of the distinctive antigenic characteristics into three major types, A, B, and C, which have shared no cross-reacting antigens.

Influenza virus is transmitted from person to person as an airborne infection. The virus may localize in the respiratory, nasal and/or bronchial tracts. Symptoms of the influenza virus can range from severe retro-orbital headache, nonbacterial pharyngitis and laryngitis to tracheobronchitis or primary viral pneumonia. Influenza infections also can be associated with several non-specific phenomena that impair antibacterial resistance factors, such as bacterial pneumonia.

Anti-influenza agents include amantadine hydrochloride. Additionally, vaccination and previous infection actively immunize against reinfection by influenza viruses with homologous or closely related surface antigens. The vaccination can be a live or killed influenza virus. Although vaccines have proven to be useful, there are still problems with vaccine production, such as the annual decision as to which antigen should be incorporated into the vaccine and how many antigens should be included.

Herpes is vital disease with no current cure. Two major antigenic forms of the herpes simples virus have been identified: herpes simplex type 1 virus (HSV-1) (oral) and herpes simplex type 2 virus (HSV-2) (genital). The genital infection due to HSV-2 is one of the most common venereal disease in the United States, reaching epidemic portions over the last decade.

A striking feature of all members of the herpes virus family is their ability to persist in a clinically quiescent or latent state. Features of HSV-1 are fever blisters, keratitis, and rarely, encephalitis. Features of HSV-2 are genital infections, such as urethritis in males and vulvitis, vaginitis, and cervicitis in females. Furthermore, a pregnant woman with an active infection at the time of delivery can transmit the virus to her newborn child.

Over the years, various substances have been postulated as medications for the various kinds of herpes. Examples include a mixture of vitamin C and vitamin P (U.S. Pat. No. 4,049,798), a mixture of kelp and a carrier (U.S. Pat. No. 4,117,120), extract of mountain ash berries (U.S. Pat. No. 4,132,782), a water soluble extract from marine red alga (U.S. Pat. No. 4,162,782), antiviral lignosulfate (U.S. Pat. No. 4,185,097), 1-amino-2,4-ethanobicyclo[3,3,1]nonane or salts thereof (U.S. Pat. No. 4,230,725), and a suspension of boric acid, tannic acid, and salicylic acid, preferably in an ethanol solvent/carrier (U.S. Pat. No. 4,285,934). Additionally, Acyclovir is an antiviral agent that has demonstrated positive therapeutic effect in the treatment of genital herpes virus infection.

Although agents are known which show at least a degree of effectiveness in inhibiting replication of these and other viruses, additional agents are sought.

Accordingly, it is an object of this invention to provide novel synthetic compounds having potent anti-viral activity. It is a further object of this invention to provide novel synthetic compounds having anti-vital activity that are not nucleotide analogs. Other objectives of this invention will become apparent from the following description and accompanying claims.

SUMMARY OF THE INVENTION

In accordance with the present invention, there are provided synthetic polymers having potent anti-viral activity. The polymers are prepared by dehydrogenative polymerization of one or more p-hydroxylated cinnamic acids or p-hydroxylated cinnamyl alcohols with a dehydrogenating agent in the presence of a hydrogen acceptor. The synthesized polymers have molecular weights within the range of 2,000 to 50,000. They show activity against a number of viruses, including HIV, influenza and herpes simplex viruses.

DETAILED DESCRIPTION OF THE INVENTION

Figure 1B:
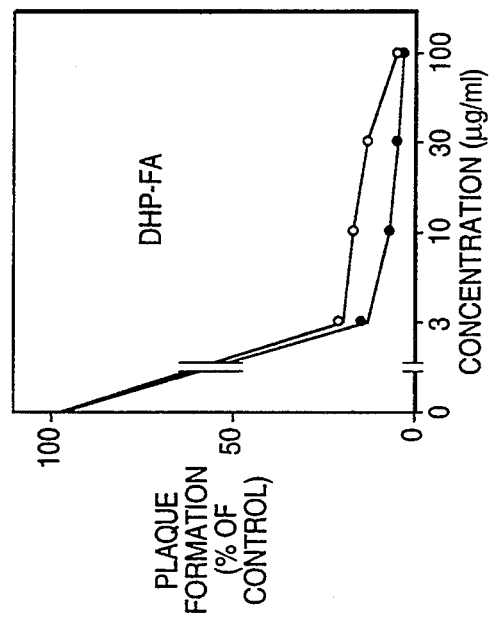
FIGS. 1A–1D represent four graphs which show the inhibition of influenza virus replication by polishers of caffeic acid, ferulic acid, p-coumaric acid and copolymers of ferulic acid and coniferyl alcohol respectively.

Suitable starting materials for the process of this invention include monomeric fortes of p-hydroxylated cinnamic acids and p-hydroxylated cinnamyl alcohols, including:

(a) caffeic acid, also known as 3-(3,4-dihydroxyphenyl)-2-propenoic acid ($C_9H_8O_4$; molecular weight 180.15);

(b) p-coumaric acid, also known as 3-(4-hydroxyphenyl)-2-propenoic acid ($C_9H_8O_3$; molecular weight 164.15);

(c) ferulic acid, also known as 3-(4-hydroxy-3-methoxyphenyl)-2-propenoic acid ($C_{10}H_{10}O_4$; molecular weight 194.18);

(d) sinapic acid, also known as 3-(4-hydroxy-3,5-dimethoxyphenyl)-2-propenoic acid ($C_{11}H_{12}O_5$; molecular weight 224.3);

(e) coniferyl alcohol, also known as 4-(3-hydroxy-1-propenyl)-2-methoxyphenol ($C_{10}H_{12}O_3$; molecular weight 180.20); and (f) sinapyl alcohol, also known as 4-(3-hydroxy-1-propenyl)-2,6-dimethoxyphenol($C_{11}H_{14}O_4$); molecular weight 210);

(g) p-coumaryl alcohol, also known as 4-(3-hydroxy-1-propenyl)phenol $C_9H_{10}O_2$; molecular weight 150); and (h) caffeyl alcohol, also known as 4-(3-hydroxy-1-propenyl)-2-hydroxyphenol ($C_9H_{10}O_3$ molecular weight 166).

Other p-hydroxylated cinnamic acid derivatives further substituted with methoxy or hydroxy groups and other p-hydroxylated cinnamyl alcohols further substituted by other methoxy or hydroxy groups also can be used as starting materials for the process of the present invention.

Preferred starting materials depend upon the virus to be treated. For example, to inhibit HIV replication, preferred starting materials are p-coumaric acid and ferulic acid. A preferred starting material for inhibiting herpes simplex activity is caffeic acid.

To make a synthetic polymer having anti-viral activity, the starting monomeric material is mixed with an aqueous liquid to form a solution having a pH in the range of about 5.0 to about 9.0, preferably in the range of about 6.0 to about 8.0, and most preferably of about 6.0. A suitable solvent, for example, is phosphate buffered saline, to which a base, such as NaOH or NaHCO$_3$, has been added. Generally, about 1 g to about 10 g of monomer is mixed with about one liter of solvent. Preferably, the concentration of the solution is about 5 g/l.

A dehydrogenating agent, such as horseradish peroxidase, laccase or sodium periodate, is dissolved in an aqueous liquid, such as phosphate buffered saline or water, to form a second solution. Generally about 0.1 mg. to about 20 mg. of dehydrogenating agent is added to about 1 liter of liquid. Preferably the concentration is about 5 mg/l. When an aqueous buffer is used, the pH of the solution desirably is substantially the same as that of the solution of monomer. As used herein, "substantially the same as" means that the pH is not more than about 1.0 unit higher or lower than the pH of the solution of monomer.

A third solution is made with a hydrogen acceptor. If the dehydrogenating agent is horseradish peroxidase, a preferred hydrogen accetor is hydrogen peroxide. If laccase is used as the dehydrogenating agent, a useful hydrogen acceptor is molecular oxygen. If a chemical oxidizing agent is used as the dehydrogenating agent, no hydrogen acceptor is required. Generally, about 0.1 g. to about 10 g. of hydrogen peroxide is mixed with 1 liter of liquid. Again, water or a suitable solvent, such as phosphate buffered aqueous solutions, the pH of which has been adjusted as necessary to be substantially the same as that of the solution of monomer, can be used as the liquid. Preferably, the concentration of the hydrogen acceptor solution is about 1 g/l.

In one embodiment of the process of this invention, the solution of the monomer is mixed with the solution of the dehydrogenating agent, then the solution of the hydrogen acceptor is added dropwise with constant stirring to the resultant solution. Desirably, the hydrogen acceptor is added to give a final concentration of about 0.1 to about 2.0 molar equivalent of hydrogen acceptor to the monomeric compound being dehydrogenated.

In an alternative embodiment, the solution of monomer and the solution of hydrogen acceptor can be added dropwise (preferably simultaneously from respective dropping funnels) to the solution of dehydrogenating agent with constant stirring to give a final concentration of 0.1 to 2 molar equivalent of dehydrogenating agent to the monomeric compound being dehydrogenated.

With either process, the reaction mixture containing the monomeric compound, hydrogen acceptor and dehydrogenating agent is stirred for about 5 to about 180 minutes, preferably for about 120 minutes, at a temperature within the range of 4° C. to about 50° C. A preferred temperature range is from about 20° C. to about 30° C. Once the reaction has gone to completion, the dehydrogenated polymers which have been formed are isolated from the reaction mixture. Isolation conveniently can be achieved by acidic precipitation, such as by adding glacial acetic acid until the pH of the reaction mixture is less than 5.0, or by lyophilization after aqueous dialysis.

Desirably, the isolated polymers then are purified, as by dissolving them in an organic solvent, such as methanol or acetone, and then filtering the resultant solution through a filter paper. The filtrate then is added dropwise to an acidic aqueous solution, such as, for example, 0.01M HCl, with constant stirring. The purified polymers then are isolated either by lyophilization or by centrifugation and subsequent vacuum drying.

The yields of the dehydrogenative polymerization of the monomers typically are in the range of about 68% to about 87%. The polymers typically have molecular weights within the range of about 2,000 to about 50,000.

Throughout this application, reference is made to polymers of p-hydroxylated cinnamic acids and p-hydroxylated cinnamyl alcohols having anti-viral activities. It is to be understood that polymerization of a single monomeric compound gives rise to homopolymers and that polymerization of two or more of the monomers will yield copolymers. Both the homopolymers and copolymers have anti-vital activity and are included within the scope of this invention. It also is to be recognized that the polymerization reaction of any monomeric compound can produce a mixture of molecules, such as 10-mers to 250-mers, to yield a final preparation with a molecular weight ranging from about 2,000 to about 50,000.

Each of the dehydrogenated polymers gives an ultraviolet (UV) spectrum showing a maximum at about 280 nm and a minimum at about 260 run, accompanied by an end-absorption in the visible region. When analyzed in an alkaline medium (pH 12), however, a shoulder appears at about 320 run due to dissociation of the phenolic group, but no appreciable change is observed when analysis is carried out in an acidic medium (pH 3–4). Infra-red (IR) spectrum of each of the synthetic polymers shows a broad and strong absorption in about 3600 $cm^{-1}$ due to hydrogen-bonded OH group, a set of peaks at about 1600 $cm^{-1}$ and about 1500 $cm^{-1}$ due to aromatic double bonds, and a peak at about 1200 $cm^{-1}$ due to C—O groups. On the nuclear magnetic resonance (NMR) spectra of each of these synthetic polymers, the signals appear as expected from the structural units: aromatic ring protons in about 8–7 ppm, aliphatic double bond protons in about 6–5 ppm, and CH protons adjacent oxygen functions in about 5–4 ppm. Polymers containing methoxy groups show an additional intense signal at about 4 ppm due to the $OCH_3$ protons.

Polymers made from hydroxylated p-cinnamic acids and hydroxylated p-cinnamyl alcohols in accordance with this invention have been found to have potent anti-HIV, anti-influenza and anti-herpes simplex virus activity as shown by assays which measure the inhibition of HIV, influenza virus or herpes simplex virus replication, respectively, in cells infected with the virus which are grown in a medium containing the polymers of this invention. HIV replication has been found to be inhibited by as much as 98%, depending upon the identity and concentration of polymer in the medium and the pH at which the polymer was made. Replication of influenza virus has been shown to be inhibited by as much as 95–98%, depending upon these same factors, and herpes simplex virus activity can be reduced to zero.

The present invention is further illustrated by the following examples, which are provided for informational purposes and are not intended to be limiting.

EXAMPLE 1

One gram of p-coumaric acid was dissolved in 5 ml of 1M NaOH and diluted to 200 ml with 0.05M phosphate buffered saline (PBS) (pH 6.0) to give a solution identified hereafter as Solution A.

Ten milligrams of horseradish peroxidase were dissolved in 200 ml of 0.05M PBS (pH 6.0) to give a solution identified hereinafter as solution B.

A third solution, identified hereinafter as solution C, was made comprising 300 ml of 0.1% (w/w) $H_2O_2$ in 0.05M PBS (pH 6.0). Each of the three solutions was prepared immediately prior to use.

Solution A and solution C were added dropwise simultaneously to solution B over a one hour period with constant stirring at room temperature to produce a preparation of polymers of p-coumaric acid. The reaction mixture was stirred for 2 hours at room temperature and then acidified by the dropwise addition of glacial acetic acid with constant stirring at room temperature to give a final pH of 3.0. The mixture was transferred to a 4° C. icebath and placed in a 4° C. refrigerator for one hour.

To recover the precipitate, the mixture was centrifuged at 10,000 xg for 10 minutes at 4° C. and the aqueous phase discarded. The pellet was washed twice with 400 ml of 0.01M HCl each time and dissolved in 80 ml of methanol and filtered with a number 2 filter (Whatmann Co., Hillsboro, Oreg.). The filtrate then was added dropwise to 800 ml of 0.01M HCl at room temperature with constant stirring.

After cooling at 4° C. for 30 minutes, the precipitate was recovered by centrifugation at 10,000 xg at 4° C. for 10 minutes. The precipitate then was washed twice with 400 ml of 0.01M HCl each time, dissolved in minimum amounts of water and lyophilized for storage until use. The molecular weight of this preparation was 2,000 to 50,000.

The polymer was tested to determine its effect on HIV replication. The anti-HIV assay was performed as described by Lai et al., AIDS *Research and Human Retroviruses* 6:205 (1990). $5 \times 10^5$ CEM cells were suspended in 1 ml of a virus preparation containing HIV-1 of NiT strain isolated from a New York patient with AIDS (AIDS *Research* 1:407 [1985]) at 37° C. for 4 hours. The infected cells were cultured at $1.5 \times 10^5$ cells/ml in medium (RPMI-1640 medium supplemented with 2% newborn calf serum, 100 units/ml penicillin and 100 µg/ml streptomycin) alone or in medium containing a final concentration of 0.3, 3.0 or 10 µg/ml of the synthesized polymer.

After incubation for 5 days at 37° C. in 100% humidified atmosphere of 5% $CO_2$, the amount of HIV-1 present in each culture was assayed by an antigen capture ELISA (Coulter Immunology, FL) which specifically quantitates the amount of HIV-1 core protein p24. The percent inhibition of HIV replication was calculated as p24 protein in cultures maintained in the presence of the compound divided by p24 concentration in culture maintained in medium alone and multiplied by 100. The results are shown in Table 1. As can be seen from the table, HIV-1 replication was inhibited by 77% when the infected cells were maintained in medium containing as little as 3 µg/ml of the synthesized polymer of p-coumaric acid.

The procedures of this example were repeated, with the only difference being that the solutions were made at a pH of 8.0. The results of the anti-HIV assays using the polymers formed at this pH also are presented in Table 1.

EXAMPLE 2

One gram of caffeic acid was dissolved in 5 ml of 1M NaOH and diluted to 200 ml with 0.05M PBS (pH 8.0) to give a solution identified hereinafter as solution A.

Ten milligrams of horseradish peroxidase was dissolved in 200 ml of 0.05M PBS (pH 8.0) to give a solution identified hereinafter as solution B.

A third solution, identified hereinafter as solution C, was made comprising 300 ml of 0.1% (w/w) $H_2O_2$ in 0.05M PBS (pH 8.0). Each of the three solutions was made immediately prior to use.

Solution A was mixed with solution B. Solution C then was added dropwise to the mixture for a period of one hour with constant stirring at room temperature to produce a preparation of polymers of caffeic acid.

The reaction mixture was stirred for 2 hours at room temperature, dialyzed against 4 changes of 2 liters of deionized water and lyophilized.

The lyophilized material was dissolved in 80 ml of methanol and filtered with a number 2 filter (Whatmann, Hillsboro, Oreg.). The filtrate then was added dropwise to 800 ml of 0.1M HCl at room temperature with constant stirring. After cooling at 4° C. for 30 minutes, the polymers were recovered, lyophilized and stored until use. The molecular weight of the polymers ranged from about 2,000 to about 50,000.

An anti-HIV assay was performed as described in Example 1. The results are provided in Table 1 below.

As can be seen from the table, HIV replication was inhibited by 83% when the infected cells were maintained in medium containing 10 μg/ml of the synthesized polymer of caffeic acid.

Polymerization of caffeic acid was repeated, using the procedures set forth in Example 1. The results of the second anti-HIV assay also are shown in Table 1.

EXAMPLE 3

The experiments set forth in example 1 were repeated with the exception that ferulic acid was used as the monomer in place of p-coumaric acid. Two sets of solutions were made which were identical, except that one set had a pH of 6.0 and the other a pH of 8.0. The dehydrogenative polymerization reaction and subsequent procedures were carried out using each set of solutions. The results of the anti-HIV assays are shown in Table 1 below.

EXAMPLE 4

The experiments set forth in Example 1 were repeated with the exception that coniferyl alcohol was used in place of p-coumaric acid. Only one set of solutions, having a pH of 6.0, was made and the dehydrogenative polymerization reaction was carried out only at pH 6.0. The results of the anti-HIV assay are shown in Table 1 below.

TABLE 1

Anti-HIV impact of polymeric caffeic acid, ferulic acid, p-coumaric acid and coniferyl alcohol

| Compounds | Percent inhibition of HIV replication by compound used at | | |
|---|---|---|---|
| | 10 | 3.0 | 0.3 μg/ml |
| p-coumaric acid | | | |
| polymer (pH 6)[1] | 98% | 77% | 39% |
| polymer (pH 8)[2] | 70% | 53% | 9% |
| polymer (pH 8)[3] | 73% | 63% | 0% |
| Caffeic acid | | | |
| polymer (pH 8)[2] | 74% | 18% | 0% |
| polymer (pH 8)[3] | 83% | 38% | 0% |
| Ferulic acid | | | |
| polymer (pH 6)[1] | 95% | 73% | 46% |
| polymer (pH 8)[2] | 74% | 5% | 11% |
| polymer (pH 8)[3] | 72% | 40% | 23% |
| Coniferyl Alcohol | | | |
| polymer (pH 6)[1] | 43% | 41% | 3% |

[1]Dehydrogenative polymerization was performed as described in example 1, in PBS at pH 6.0
[2]Dehydrogenative polymerization was performed as described in example 1, in PBS at pH 8.0
[3]Dehydrogenative polymerization was performed as described in Example 2, in PBS at pH 8.0

EXAMPLE 5

Polymers from caffeic acid (DHP-CA), ferulic acid (DHP-FA), p-coumaric acid (DHP-pCA), and a co-polymer of coniferyl alcohol and ferulic acid (DHP-FA.C) were prepared by dehydrogenative polymerization in accordance with the procedures of each of examples 1 and 2. (To make the co-polymer, solution A was made using 0.5 g coniferyl alcohol and 0.5 g ferulic acid.) The anti-influenza virus activity of each polymer was tested in the MDCK cell line (American Tissue Culture Collection; CCL 34) as described by Nagata and co-workers (*Antiviral Research*, 13:11–22, 1990). The MDCK cells were grown in Minimal Essential Medium supplemented with 10% fetal calf serum. Confluent monolayer culturs of MDCK cells in 60 mm plastic dishes were exposed to doses of 200 pfu of influenza virus A/PR/B/34 (H1N1) for 30 minutes at 37° C. The infected cells were then washed with medium to remove the unabsorbed virus and overlayered with fresh medium containing 0.8% agarose, 0.2% bovine serum albumin, 4μ/ml trypsin and 0, 3, 10, 30 or 100 μg/ml of a polymer.

Figure 1D:
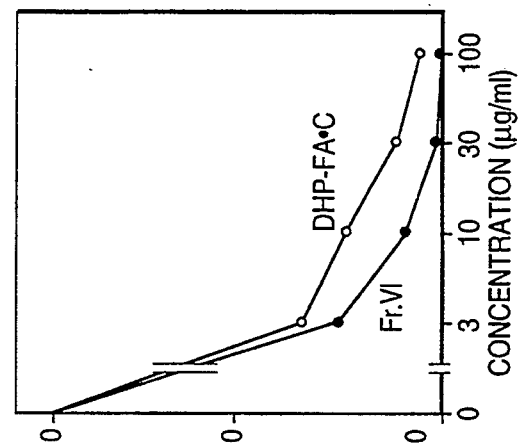
Figure 1A:
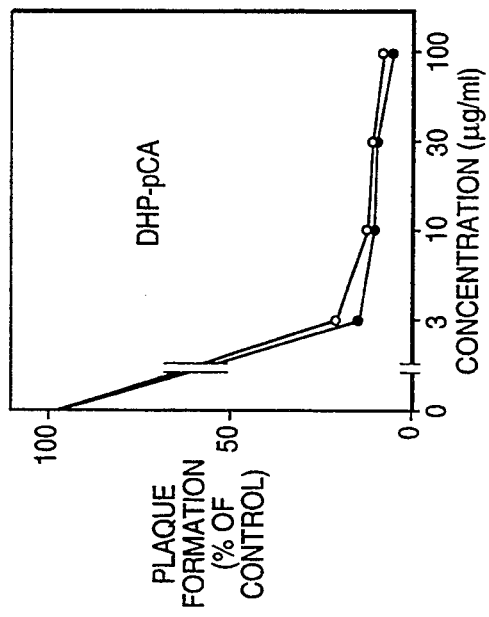
Figure 1C:
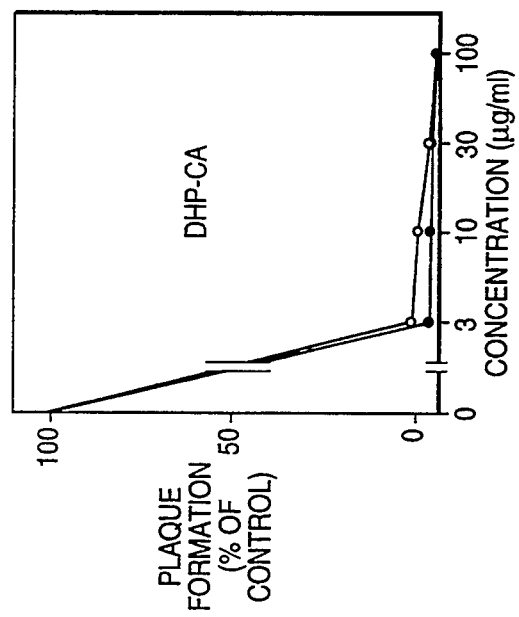

As shown in FIG. 1, caffeic acid polymer (DHP-CA), ferulic acid polymer (DHP-FA), p-coumaric acid polymer (DHP-pCA) and copolymer of ferulic acid and coniferyl alcohol ( DHP-FA. C ) prepared according to example 1 ( solid circles ) and example 2 (opened circles) were effective against influenza vital replication and reduced the number of virus plaques seen in the infected MDCK cell cultures in a dose dependent manner. In the absence of polymer (0 μg/ml), the infection by influenza virus gave 109 virus plaques. Results in FIG. 1 are given as percent of virus plaques formed in presence of polymer (μg/ml).

EXAMPLE 6

Polymers from caffeic acid, ferulic acid and p-coumaric acid were prepared by dehydrogenative polymerization as describedin each of examples 1 and 2. The anti-herpes simplex virus activity of each polymer was tested in the HEL cell line (American Tissue Culture Collection; CCL 137). Monolayer cultures of HEL cells were maintained in medium 199 containing 1% fetal calf serum in 35 mm plastic dishes. The type-1 herpes simplex virus was a gift form Dr. Bernard Roizman (University of Chicago). The type-1 herpes simplex virus at 200 plaque forming units per ml was incubated for 1 hour with 3 μg or 10 μg per ml of a polmer. An alliquot of virus at the same infectious dose was incubated in medium as control. The preparations were used to infect the HEL cells at 37° C. for 1 hr. After infection, each culture was washed with medium to remove the unabsorbed virus. The infected cells were cultured for 16 hours in medium alone (control) or in medium containing the appropriate concentration of the polymer. Test and control cultures were performed in triplicate. The number of plaques formed in each culture was then counted. Table 2 below shows that the polymer inhibited herpes simplex virus replication, and that the polymer of caffeic acid had the highest anti-herpes simplex activity.

TABLE 2

Anti-*Herpes Simplex* Virus Activity of Polymers

| Treatment | Concentration μg/ml | *Herpes simplex* virus plaques per culture |
|---|---|---|
| No treatment | | 163 |
| | | 169 |
| Caffeic acid polymer | 3 | 46 |
| | | 53 |
| | 10 | 0 |
| | | 0 |
| p-Coumaric acid polymer | 3 | 121 |
| | | 120 |
| | 10 | 7 |
| | | 3 |
| Ferulic acid polymer | 3 | 159 |
| | | 147 |
| | 10 | 13 |
| | | 9 |

We claim:

1. A method for inhibiting replication of HIV in human cells infected with the virus which comprises contacting the cells in vitro with polymers of p-hydroxylated cinnamic acid or polymers of substituted p- hydroxylated cinnamic acid wherein the substituent is selected from the group consisting of methoxy and hydroxy groups, said polymers having molecular weights within the range of about 2,000 to about 5,000 and anti-HIV activity.

2. A method in accordance with claim 1, wherein the polymer of substituted p-hydroxylated cinnamic acid is ferrulic acid.

3. A method in accordance with claim 1, wherein the polymer of substituted p-hydroxylated cinnamic acid is caffeic acid.

4. A method in accordance with claim 1, wherein the polymer of substituted p-hydroxylated cinnamic acid is sinapic acid.

5. A method in accordance with claim 1, wherein the cells are contacted with polymers of coumaric acid.

* * * * *

UNITED STATES PATENT AND TRADEMARK OFFICE
CERTIFICATE OF CORRECTION

PATENT NO. : 5,346,695
DATED : September 13, 1994
INVENTOR(S) : Meihan Nonoyama et al.

It is certified that error appears in the above-indentified patent and that said Letters Patent is hereby corrected as shown below:

```
Col. 2, line 5, "vital" should be --
viral --; Col. 3, line 5, "fortes" should be -- forms --; Col.
5, line 3, "run" should be -- nm --; Col. 9, line
4, "5,000" should be -- 50,000 --.
```

Signed and Sealed this

Twenty-ninth Day of November, 1994

Attest:

BRUCE LEHMAN

*Attesting Officer*  *Commissioner of Patents and Trademarks*